United States Patent
Kim et al.

(10) Patent No.: US 11,839,486 B2
(45) Date of Patent: Dec. 12, 2023

(54) DEVICE AND METHOD FOR CONTROLLING THERMOTHERAPEUTIC APPARATUS HAVING FUNCTION OF MEASURING HEART RATE

(71) Applicant: CERAGEM CO., LTD., Cheonan-si (KR)

(72) Inventors: Ki Sung Kim, Cheonan-si (KR); Dong Myoung Lee, Asan-si (KR); Sang Cheol Han, Cheonan-si (KR); Sang Hee Kim, Cheonan-si (KR)

(73) Assignee: CERAGEM CO., LTD., Cheonan-si (KR)

( * ) Notice: Subject to any disclaimer, the term of this patent is extended or adjusted under 35 U.S.C. 154(b) by 1072 days.

(21) Appl. No.: 16/264,994

(22) Filed: Feb. 1, 2019

(65) Prior Publication Data

US 2019/0307395 A1 Oct. 10, 2019

(30) Foreign Application Priority Data

Apr. 5, 2018 (KR) .......................... 10-2018-0039792

(51) Int. Cl.
*A61H 15/02* (2006.01)
*A61B 5/00* (2006.01)
(Continued)

(52) U.S. Cl.
CPC .......... *A61B 5/4836* (2013.01); *A61B 5/1102* (2013.01); *A61B 5/4809* (2013.01);
(Continued)

(58) Field of Classification Search
CPC ........ A61H 2201/10; A61H 2201/0207; A61H 2230/065; A61B 5/4809; A61B 5/1102;
(Continued)

(56) References Cited

U.S. PATENT DOCUMENTS 5,993,401 A * 11/1999 Inbe ...................... A61M 21/00
601/84
6,123,661 A * 9/2000 Fukushima ........... A61M 21/00
600/26
(Continued)

FOREIGN PATENT DOCUMENTS

| CN | 102499866 A | 6/2012 |
| CN | 107157702 A | 9/2017 |

(Continued)

OTHER PUBLICATIONS

English translation of WO-2008038501-A1. (Year: 2008).*
(Continued)

*Primary Examiner* — Justine R Yu
*Assistant Examiner* — Christopher E Miller
(74) *Attorney, Agent, or Firm* — Rothwell, Figg, Ernst & Manbeck, P.C.

(57) ABSTRACT

Disclosed are a thermotherapeutic apparatus having a function of measuring a heart rate and a method of controlling the same. The thermotherapeutic apparatus includes a pretreatment portion which extracts a ballistocardiogram signal sensed by a weight detecting sensor, a heartbeat signal extractor which extracts a heartbeat signal from the pretreated signal, and a mode performer which performs control to calculate a heart rate on the basis of the extracted heartbeat signal, to determine a massage mode according to the calculated heart rate, and to automatically set a massage pattern, a massage level, and a massage temperature of the corresponding massage mode so as to perform the corresponding massage mode.

10 Claims, 4 Drawing Sheets

(51) Int. Cl.
*A61B 5/11* (2006.01)
*A61F 7/08* (2006.01)
*A61H 23/00* (2006.01)

(52) U.S. Cl.
CPC .............. *A61B 5/7278* (2013.01); *A61F 7/08* (2013.01); *A61H 23/006* (2013.01); *A61H 2201/10* (2013.01); *A61H 2230/065* (2013.01)

(58) Field of Classification Search
CPC .......... A61M 21/02; A61M 2021/0022; A61M 2021/0066
See application file for complete search history.

(56) References Cited

U.S. PATENT DOCUMENTS

| | | | |
|---|---|---|---|
| 6,542,779 B1 * | 4/2003 | Lee | A61F 7/02 607/90 |
| 6,643,551 B1 * | 11/2003 | Park | A61N 5/06 607/96 |
| 10,842,708 B2 * | 11/2020 | Le | A61H 15/0078 |
| 2004/0225239 A1 * | 11/2004 | Yamamoto | A61H 15/0078 601/84 |
| 2004/0245036 A1 * | 12/2004 | Fujita | B60N 2/002 180/272 |
| 2007/0083079 A1 * | 4/2007 | Lee | A61B 5/4806 600/27 |
| 2009/0276062 A1 | 11/2009 | Kanai et al. | |
| 2010/0210921 A1 * | 8/2010 | Park | A61B 5/0205 600/301 |
| 2010/0249613 A1 * | 9/2010 | Hashimoto | A61M 21/02 600/485 |
| 2012/0071792 A1 * | 3/2012 | Pfeffer | A61B 5/11 600/587 |
| 2013/0158415 A1 * | 6/2013 | Kim | A61B 5/1116 600/483 |
| 2014/0179986 A1 * | 6/2014 | Kelley | A61B 5/4806 600/26 |
| 2014/0371638 A1 * | 12/2014 | Lee | A61H 15/0078 601/18 |
| 2015/0366746 A1 * | 12/2015 | Ashby | G16H 40/63 601/49 |
| 2016/0346501 A1 * | 12/2016 | Hooper | A61B 5/02438 |
| 2017/0160709 A1 * | 6/2017 | Yang | G16H 40/63 |
| 2017/0296775 A1 * | 10/2017 | Mayo | G16H 20/30 |
| 2017/0308046 A1 * | 10/2017 | Li | G05B 19/042 |
| 2017/0312161 A1 | 11/2017 | Johnson et al. | |
| 2017/0340270 A1 * | 11/2017 | Ganesh | A61H 23/02 |
| 2018/0256432 A1 * | 9/2018 | Mayo | A61H 1/00 |
| 2018/0336968 A1 * | 11/2018 | Hwang | A61B 5/16 |
| 2019/0160253 A1 * | 5/2019 | Bae | A61H 15/02 |
| 2019/0209843 A1 * | 7/2019 | Park | G16H 20/00 |
| 2021/0219737 A1 * | 7/2021 | Youngblood | A61B 5/4809 |

FOREIGN PATENT DOCUMENTS

| | | | | |
|---|---|---|---|---|
| EP | 2201922 A1 * | 6/2010 | .......... | A61H 9/0078 |
| JP | 2007-289401 A | 11/2007 | | |
| JP | 2010148561 A | 7/2010 | | |
| JP | 2012-239629 A | 12/2012 | | |
| KR | 20170049171 A | 5/2017 | | |
| KR | 10-1744691 B1 | 6/2017 | | |
| KR | 10-1781953 B1 | 9/2017 | | |
| KR | 101780304 B1 * | 10/2017 | .......... | A61H 9/0078 |
| WO | WO-2014050005 A1 * | 4/2014 | ........ | A61H 33/0095 |

OTHER PUBLICATIONS

English translation of WO-2014106716-A1. (Year: 2014).*
English translation of JP 2003010230 A (Year: 2003).*
Indian Office Action cited in Application No. 201924012655 dated Apr. 12, 2021, 7 pages.

* cited by examiner

DEVICE AND METHOD FOR CONTROLLING THERMOTHERAPEUTIC APPARATUS HAVING FUNCTION OF MEASURING HEART RATE

CROSS-REFERENCE TO RELATED APPLICATION

This application claims priority to and the benefit of Korean Patent Application No. 2018-0039792, filed on Apr. 5, 2018, the disclosure of which is incorporated herein by reference in its entirety.

BACKGROUND

1. Field of the Invention

The present invention relates to a thermotherapeutic apparatus, and more particularly, to a device and a method of controlling a thermotherapeutic apparatus having a function of measuring a heart rate which actively performs a massage mode according to a heart rate of a user.

2. Discussion of Related Art

Generally, since heart rate variability provides a quantitative index for evaluating a pathological and physiological state of a cardiovascular system and receives influences of a sympathetic nervous system and a parasympathetic nervous system, heart rate variability may be used as a quantitative index for an automatic nervous system related to a stress disease. Accordingly, products such as health equipment, massagers, thermotherapeutic apparatuses, and the like which are driven in relation to cardiac impulse have appeared.

However, since a massager or a thermotherapeutic apparatus including a massage function accompanies vibration caused by massages, it is difficult to precisely measure cardiac impulse such that application thereof is limited. In addition, a thermotherapeutic apparatus which actively performs a massage mode according to a heart rate is necessary.

Additionally, although a conventional thermotherapeutic apparatus detects whether a user is present by using a weight thereof, when whether a user is present is detected simply by a weight, objects having a weight similar to that of a human being is misinterpreted to be a human being so as to cause an unnecessary massage operation.

RELATED ART DOCUMENT

Patent Document (Patent Document 0001) JP No. 2010-148561 A

SUMMARY OF THE INVENTION

The present invention is directed to providing a device and a method for controlling a thermotherapeutic apparatus having a function of measuring a heart rate and capable of measuring a heart rate by using a weight detecting sensor for sensing a weight of a user and actively performing a massage mode according thereto.

The present invention is also directed to providing a device and a method for controlling a thermotherapeutic apparatus capable of precisely determining whether a user is present according to whether a heart rate is calculated.

According to one aspect of the present invention, a control device for a thermotherapeutic apparatus having a function of measuring a heart rate includes a pretreatment portion which pretreats a ballistocardiogram signal sensed by a weight detecting sensor, a heartbeat signal extractor which extracts a heartbeat signal from the pretreated signal, and a mode performer which performs control to calculate a heart rate on the basis of the extracted heartbeat signal, to determine a massage mode according to the calculated heart rate, and to automatically set a massage pattern, a massage level, and a massage temperature of the corresponding massage mode so as to perform the corresponding massage mode.

The control device may further include a setting portion through which at least one of user information and operation settings is input and a storage which stores a reference heart rate according to an age and gender of a user and a massage temperature, a massage pattern, and a massage level according to each massage mode. Here, the input user information may include an age and gender.

The pretreatment portion may repetitively amplify and filter out the ballistocardiogram signal, and the heartbeat signal extractor may extract the heartbeat signal by sampling and filtering out the pretreated signal.

The mode performer may perform a parasympathetic-stimulating mode which activates a parasympathetic nervous system by setting the massage temperature to be a first reference temperature and setting the massage pattern and the massage level to be a massage pattern and a massage level which are preset to stimulate the parasympathetic nervous system when the calculated heart rate is more than the reference heart rate, may perform a sympathetic-stimulating mode which activates a sympathetic nervous system by setting the massage temperature to be a second reference temperature higher than or equal to the first reference temperature and setting the massage pattern and the massage level to be a massage pattern and a massage level which are preset to stimulate the sympathetic nervous system when the calculated heart rate is less than the reference heart rate, may perform a standard mode which operates in a state set immediately prior to when the calculated heart rate is equal to the reference heart rate, and may control a driving module and a transfer motor to perform each of the above massage modes.

The mode performer may determine whether the user is asleep on the basis of the calculated heart rate while performing a massage and may control a driving module and a transfer motor to perform a sleep mode which induces a deep sleep by setting the massage temperature, the massage pattern, and the massage level to be a massage temperature, a massage pattern, and a massage level which are preset for inducing a deep sleep when it is determined that the user is asleep.

The mode performer may control such that a massage is automatically initiated depending on whether the heart rate is calculated or not.

According to another aspect of the present invention, a method of controlling a thermotherapeutic apparatus having a function of measuring a heart rate includes sensing a ballistocardiogram signal by using a weight detecting sensor, pretreating the sensed ballistocardiogram signal, extracting a heartbeat signal from the pretreated signal, calculating a heart rate on the basis of the extracted heartbeat signal, determining a massage mode according to the calculated heart rate, and controlling to perform the corresponding massage mode by automatically setting a massage pattern, a massage level, and a massage temperature.

The method may further include inputting at least one of user information and operation settings. Here, the user information may include an age and gender.

The pretreating may include repetitively amplifying and filtering out the ballistocardiogram signal, and the extracting may include extracting the heartbeat signal by sampling and filtering out the pretreated signal.

The controlling may include performing a parasympathetic-stimulating mode which activates a parasympathetic nervous system by setting the massage temperature to be a first reference temperature and setting the massage pattern and the massage level to be a massage pattern and a massage level which are preset to stimulate the parasympathetic nervous system when the calculated heart rate is more than a reference heart rate according to the input age and gender of the user, performing a sympathetic-stimulating mode which activates a sympathetic nervous system by setting the massage temperature to be a second reference temperature higher than or equal to the first reference temperature and setting the massage pattern and the massage level to be a massage pattern and a massage level which are preset to stimulate the sympathetic nervous system when the calculated heart rate is less than the reference heart rate, and performing a standard mode which operates in a state set immediately prior to when the calculated heart rate is equal to the reference heart rate. Here, each performing operation may include controlling a driving module and a transfer motor to perform the set massage mode.

The method may further include determining whether the user is asleep on the basis of the calculated heart rate while performing a massage and controlling to perform a sleep mode which induces a deep sleep by setting the massage temperature, the massage pattern, and the massage level to be a massage temperature, a massage pattern, and a massage level which are preset for inducing a deep sleep when it is determined that the user is asleep.

The controlling may include controlling to automatically initiate a massage depending on whether the heart rate is calculated.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
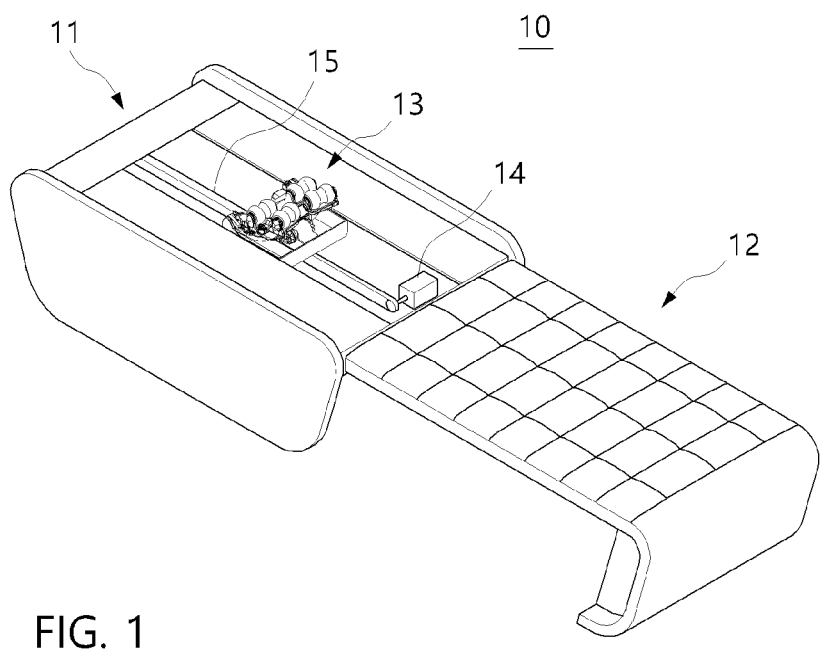
FIG. 1 is a perspective view illustrating a thermotherapeutic apparatus according to an embodiment of the present invention.

Hereinafter, an embodiment of the present invention will be described in detail with reference to the attached drawings to allow one of ordinary skill in the art to easily perform it. The present invention may be embodied in a variety of different shapes and is not limited to the embodiment disclosed herein. In order to clearly describe the present invention, parts irrelevant to the present invention are omitted throughout the drawings, and equal or similar components are referred to as equal reference numerals.

Figure 2:
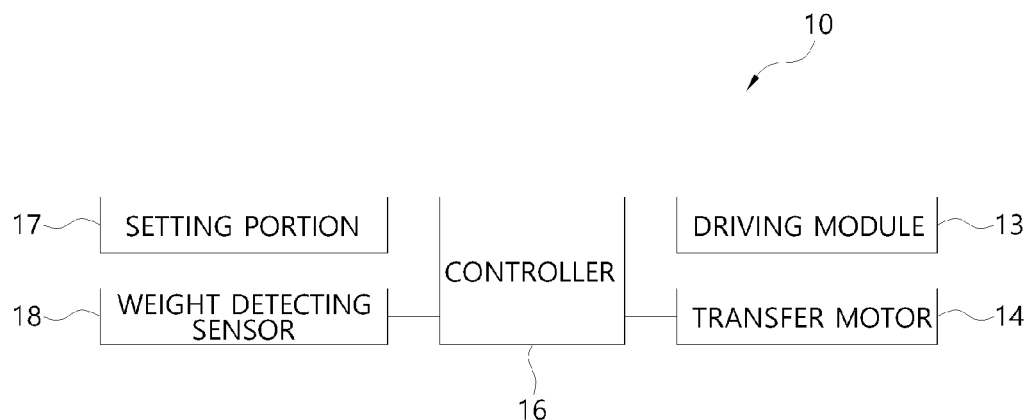
FIG. 2 is a block diagram schematically illustrating the thermotherapeutic apparatus of FIG. 1.

Hereinafter, a control device of a thermotherapeutic apparatus according to an embodiment of the present invention will be described in detail with reference to the drawings. FIG. 1 is a perspective view illustrating a thermotherapeutic apparatus according to an embodiment of the present invention, and FIG. 2 is a block diagram schematically illustrating the thermotherapeutic apparatus of FIG. 1.

Referring to FIG. 1, a thermotherapeutic apparatus 10 including a control device 100 according to one embodiment of the present invention may include an upper body 11, a lower body 12, a driving module 13, a transfer motor 14, and a transfer means 15.

Here, the thermotherapeutic apparatus 10 is an apparatus capable of massages and a thermal therapy by using thermal ceramics on body parts of a human being and may be an apparatus for repetitively vibrating or tapping while moving over body parts of a user by using the driving module 13 and the transfer motor 14 and is not limited to a particular shape.

Also, the thermotherapeutic apparatus 10 includes a bed type on which a user lies down and receives massages or a chair type in which the user is seated and receives massages but is not limited thereto.

The upper body 11 and the lower body 12 may be arranged in parallel. The upper body 11 may include the driving module, which includes an empty space in a part thereof, the transfer motor 14, and the transfer means 15. The lower body 12 may slide from the upper body toward one side.

The driving module 13 may perform at least one of massages and a thermal therapy for each body part of the user. Here, the driving module 13 may include a ceramic member. Here, the ceramic member may include a heating source. The driving module 13 may be moved by the transfer motor 14 and the transfer means 15 in one direction in the upper body 11. Also, a height of a part of the driving module 13 which comes into contact with a body may be adjusted according to a massage level.

Referring to FIG. 2, the thermotherapeutic apparatus 10 may further include a controller 16, a setting portion 17, and a weight detecting sensor 18.

The controller 16 may control settings and performance of a massage mode of the thermotherapeutic apparatus 10. Here, the controller 16 may control the driving module 13 and the transfer motor 14 according to a set massage mode.

Here, the massage mode may include a massage pattern, a massage level, and a massage temperature. In more detail, the controller 16 may control the driving module 13 and the transfer motor 14 according to the massage pattern and may control the driving module 13 according to the massage level and the massage temperature.

User information may be input by the user through the setting portion 17. Here, the input user information may include age and gender. Also, a preferred massage mode may be set by the user through the setting portion 17. Here, the set massage mode may include at least one of the massage temperature, the massage pattern, and the massage level.

The weight detecting sensor 18 may be included in the driving module 13 to sense a weight of the user. As an example, the weight detecting sensor 18 may be a load cell.

The weight detecting sensor 18 may sense a weight signal including a micro ballistocardiogram signal. Here, the ballistocardiogram signal is a signal obtained by sensing vibration of the body which accompanies a heartbeat.

Figure 3:
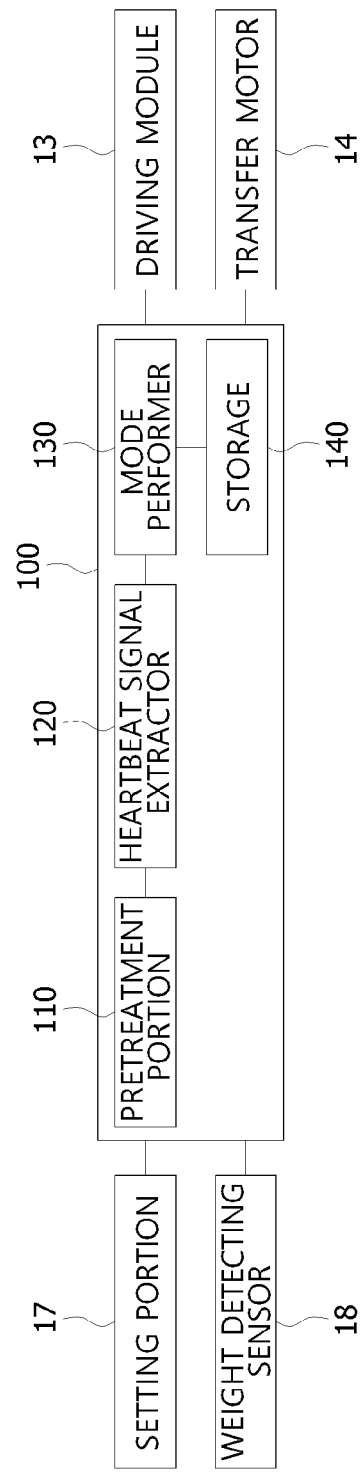
FIG. 3 is a block diagram illustrating a control device of the thermotherapeutic apparatus having a function of measuring a heart rate according to the embodiment of the present invention.

The above-described control device 100, which controls thermotherapeutic apparatus 10, will be described in more detail. FIG. 3 is a block diagram illustrating the control device of the thermotherapeutic treatment apparatus having a function of measuring a heart rate according to the embodiment of the present invention.

The control device 100 of the thermotherapeutic apparatus includes a pretreatment portion 110, a heartbeat signal extractor 120, a mode performer 130, and a storage 140. Here, the control device 100 of the thermotherapeutic apparatus is for more actively controlling the thermotherapeutic apparatus 10 by recognizing a state of the user through a heart rate thereof.

The pretreatment portion 110 may perform pretreatment to remove noise from a ballistocardiogram signal sensed by the weight detecting sensor 18. Here, generally, the weight detecting sensor 18 is included in the thermotherapeutic apparatus 10 for the purpose of sensing a weight or a body pressure of the user. The present invention may sense a ballistocardiogram signal by using the weight detecting sensor 18.

Here, the ballistocardiogram signal detected by the weight detecting sensor 18 is a micro signal included in a weight signal. Accordingly, in order to extract a micro ballistocardiogram signal, it is necessary to remove not only power noise but also the weight signal and other noises.

To this end, the pretreatment portion 110 may repetitively amplify and filter out the ballistocardiogram signal sensed by the weight detecting sensor 18. The pretreatment portion 110 will be described below with reference to FIG. 4.

The heartbeat signal extractor 120 may extract a heartbeat signal from a signal pretreated by the pretreatment portion 110. Here, the heartbeat signal extractor 120 may extract the heartbeat signal by sampling and filtering out the pretreated heartbeat signal. The heartbeat signal extractor 120 will be described below with reference to FIG. 5.

The mode performer 130 may calculate a heart rate on the basis of a heartbeat signal extracted by the heartbeat signal extractor 120. As an example, the mode performer 130 may calculate a heart rate on the basis of the number of peak points of a heartbeat signal extracted for a certain period of time.

Also, the mode performer 130 may perform control such that massage is automatically initiated according to whether a heart rate is calculated. Here, the mode performer 130 may distinguish a state in which objects having a certain weight are disposed on the thermotherapeutic apparatus 10 from a state in which a human being lies down thereon according to sensing of a heart rate. Here, the mode performer 130 may precisely determine whether the user lies down on the thermotherapeutic apparatus 10 to receive massage and may automatically initiate massage. Accordingly, it is possible to prevent an error of sensing an object as a human being simply due to a weight thereof.

Also, the mode performer 130 may determine a massage mode according to the calculated heart rate. Here, the mode performer 130 may determine a state of the user according to the heart rate and may automatically set a massage mode capable of relaxing the state of the user.

Here, the mode performer 130 may control such that a massage pattern, a massage level, and a massage temperature of the corresponding massage mode are automatically set to activate a sympathetic nervous system or a parasympathetic nervous system, and the corresponding massage mode is actively performed.

As an example, when a calculated heart rate is more than a reference heart rate according to an input age and gender of the user, the mode performer 130 may perform a parasympathetic-stimulating mode which activates a parasympathetic nervous system of the user to stabilize body rhythms Here, the reference heart rate may be a resting heart rate with respect to the age and gender input by the user through the setting portion 17.

Here, the mode performer 130 may set the massage temperature to be a first reference temperature to activate the parasympathetic nervous system. Here, the first reference temperature may be a temperature at which the parasympathetic nervous system is vigorously activatable.

Also, the mode performer 130 may set the massage pattern and the massage level to be a massage pattern and a massage level which are preset to stimulate the parasympathetic nervous system. As an example, the mode performer 130 may set the massage pattern to intensively massage a natal part (an end of a spinal cord) and a back part of a neck (a midbrain, a bulb of a spinal cord, and the like). Here, the natal part corresponds to the end of the spinal cord, and the back part of the neck corresponds to the midbrain or the bulb of the spinal cord in which the parasympathetic nervous system is located. Accordingly, the mode performer 130 may stimulate the parasympathetic nervous system by controlling to perform a massage on the corresponding part.

Also, when the calculated heart rate is less than the reference heart rate according to the input age and gender of the user, the mode performer 130 may perform a sympathetic-stimulating mode which activates a sympathetic nervous system of the user to activate body rhythms.

Here, the mode performer 130 may set the massage temperature to be a second reference temperature to activate the sympathetic nervous system. Here, the second reference temperature may be a temperature at which the sympathetic nervous system is vigorously activatable. Here, the second reference temperature may be higher than or equal to the first reference temperature.

Also, the mode performer 130 may set the massage pattern and the massage level to be a massage pattern and a massage level which are preset to stimulate the sympathetic nervous system. As an example, the mode performer 130 may set the massage pattern to intensively massage a spine (a middle of the spinal cord). Here, the spine corresponds to the middle of the spinal cord in which the sympathetic nervous system is located. Accordingly, the mode performer 130 may stimulate the sympathetic nervous system by controlling to perform a massage on the corresponding part.

Here, the mode performer 130 may set the same massage level with respect to a massage part.

Also, when the calculated heart rate is equal to the reference heart rate according to the input age and gender of the user, the mode performer 130 may perform a standard mode which operates a massage mode set immediately prior.

Here, the mode performer 130 may perform a massage and a thermal therapy in a massage mode set by a current user or set by a previous user to use the thermotherapeutic apparatus 10.

Here, the mode performer 130 may control the driving module 13 and the transfer motor 14 to perform a massage mode determined according to a heart rate of the user.

Meanwhile, the user may sleep while using the thermotherapeutic apparatus 10. Here, thermotherapeutic apparatus 10 may operate in a massage mode used immediately prior which may act as a factor interfering in sleeping according to circumstances.

To this end, according to the embodiment of the present invention, a massage mode may be automatically adjusted to induce the user to sleep well when the user is asleep while using the thermotherapeutic apparatus 10.

That is, the mode performer 130 may determine whether the user is asleep on the basis of a heart rate calculated while performing a massage. As an example, when the heart rate calculated while performing the massage is reduced to a certain level, the mode performer 130 may determine that the user is asleep.

Here, when the user is asleep, the mode performer 130 may perform a sleep mode which induces a deep sleep. Here, the mode performer 130 may set the massage temperature, the massage pattern, and the massage level to be a massage temperature, a massage pattern, and a massage level which are preset to induce a deep sleep.

As an example, the mode performer 130 may set the massage temperature to be the first reference temperature, set the massage level to be lower than a massage level immediately prior, and set the massage pattern to maintain a massage pattern immediately prior or to be a massage pattern of the parasympathetic-stimulating mode.

Here, the mode performer 130 may finish the sleep mode after a certain period of time has passed. Also, when the massage pattern immediately prior is maintained, the mode performer 130 may finish the sleep mode after a residual time of the corresponding massage pattern has passed. Here, the thermotherapeutic apparatus 10 may finish a massage operation.

Here, a massage temperature, a massage pattern, and a massage level of each performance mode have been described as being set according to a massage mode for each state stored in the storage 140 but are not limited thereto and may be directly set by the user through the setting portion 17.

The storage 140 may store the reference heart rate according to the age and gender of the user. As an example, the reference heart rate may be a value set for each age and gender within a range of an average value (61 to 79 bpm) of a 20 to 59 year-old adult on the basis of health statistical reports. Here, the reference heart rate may be changed according to applied health statistical data.

Meanwhile, the reference heart rate is to be applied to an initial use but is not limited thereto and may be set for each user according to use of the thermotherapeutic apparatus 10 by the user. To this end, the mode performer 130 may accumulate and store the calculated heart rates in the storage 140 and may calculate a heart rate for each user on the basis thereof. Here, the mode performer 130 may accumulatively learn and compile statistics of the calculated heart rate for each user so as to replace the reference heart rate of the storage 140.

Also, the storage 140 may store a massage temperature, a massage pattern, and a massage level which are preset according to each massage mode. Here, at least one of a massage temperature, a massage pattern, and a massage level which are preset for a massage may be set by the user.

Figure 4:
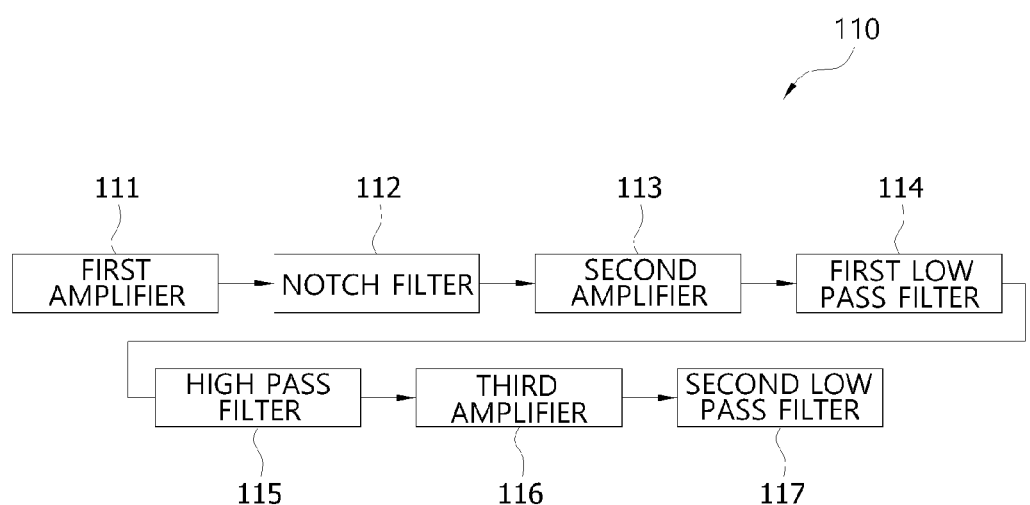
FIG. 4 is a block diagram illustrating detailed components of a pretreatment portion in FIG. 3.

FIG. 4 is a block diagram illustrating detailed components of the pretreatment portion in FIG. 3.

The pretreatment portion 110 may include a first amplifier 111, a notch filter 112, a second amplifier 113, a first low pass filter 114, a high pass filter 115, a third amplifier 116, and a second low pass filter 117.

The first amplifier 111 may primarily amplify a ballistocardiogram signal sensed by the weight detecting sensor 18 for filtering. Here, since the ballistocardiogram signal sensed by the weight detecting sensor 18 is a micro signal at a low level, the first amplifier 111 may amplify the signal to process the signal.

The notch filter 112 may remove power noise from the signal amplified by the first amplifier 111. To this end, the notch filter 112 may have a cutoff frequency corresponding to a frequency of power of the notch filter 112. As an example, the notch filter 112 may be a notch filter of 50 Hz or 60 Hz.

The second amplifier 113 may amplify the power noise-removed signal. Here, due to the removal of the power noise, a level of the notch-filtered signal is decreased. Accordingly, the second amplifier 113 may amplify the signal again for subsequent filtering.

The first low pass filter 114 may remove high frequency noise from the power noise-removed signal. As an example, the first low pass filter 114 may be a low pass filter of 20 Hz. Here, a low pass-filtered signal is a weight signal of the user which includes a very feeble ballistocardiogram signal.

The high pass filter 115 may remove an offset caused by the weight signal from a high frequency noise-removed signal and may extract a micro ballistocardiogram signal therefrom. As an example, the high pass filter 115 may be a high pass filter of 0.1 Hz.

The third amplifier 116 may amplify the extracted micro ballistocardiogram signal. Here, only the micro-level ballistocardiogram signal is left according to removal of the weight signal. Accordingly, the third amplifier 116 may amplify the signal again for next filtering.

The second low pass filter 117 may remove high frequency noise from the amplified ballistocardiogram signal. As an example, the second low pass filter 117 may be a low pass filter of 20 Hz.

Figure 5:
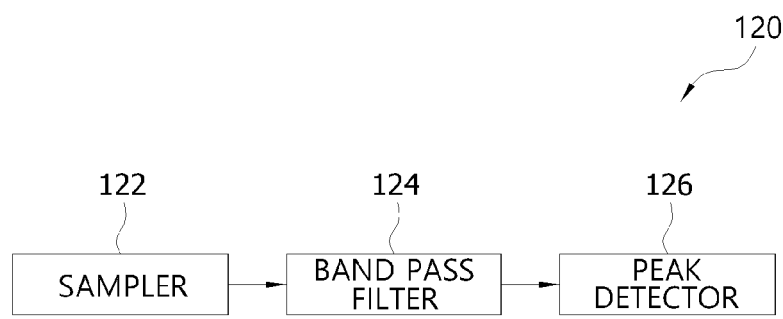
FIG. 5 is a block diagram illustrating detailed components of a heart rate extractor in FIG. 3.

FIG. 5 is a block diagram illustrating detailed components of the heartbeat signal extractor in FIG. 3.

The heartbeat signal extractor 120 may include a sampler 122, a band pass filter 124, and a peak detector 126.

The sampler 122 may sample an extracted ballistocardiogram signal. Here, since a pretreated ballistocardiogram signal is an analog signal, sampling may be performed to convert the analog signal into a digital signal. As an example, the sampler 122 may sample an extracted ballistocardiogram signal at 120 Hz.

The band pass filter 124 may filter out a frequency band corresponding to a heartbeat signal from the sampled ballistocardiogram signal. As an example, the band pass filter 124 may be a high pass filter of 1 to 47.5 Hz.

The peak detector 126 may detect a peak from the filtered ballistocardiogram signal. Here, a peak signal may correspond to a heartbeat signal.

Due to the above-described components, the control device 100 of the thermotherapeutic apparatus according to the embodiment of the present invention may relax a current state of the user to actively perform a massage and may more precisely determine whether a user is present in comparison to a case of determining whether a human being is present by using only a weight thereof so as to prevent an unnecessary malfunction.

Figure 6:
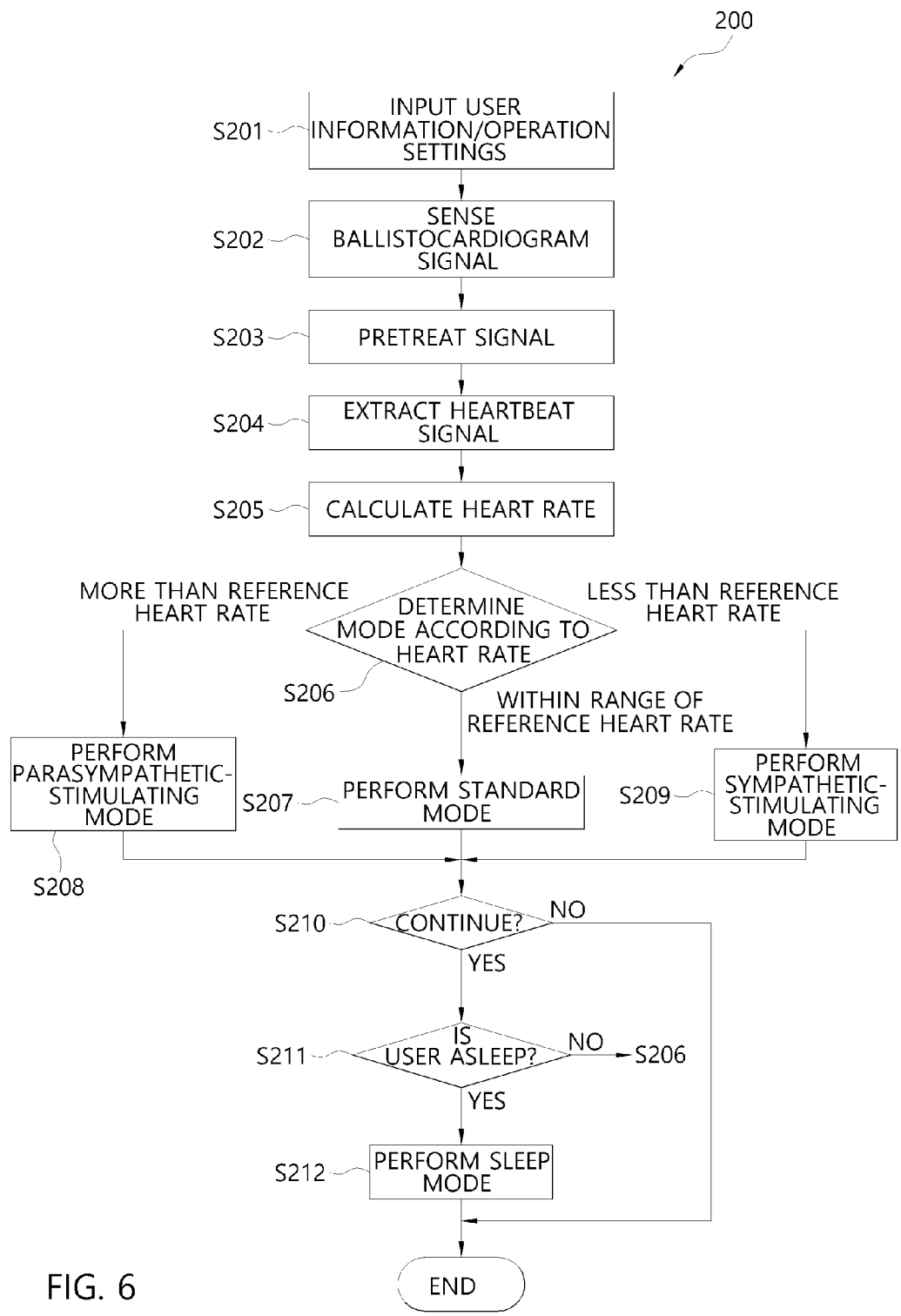
FIG. 6 is a flowchart illustrating a method of controlling a thermotherapeutic apparatus having a function of measuring a heart rate according to an embodiment of the present invention.

Hereinafter, a method of controlling a thermotherapeutic apparatus having a function of measuring a heart rate according to an embodiment of the present invention will be described with reference to FIG. 6. FIG. 6 is a flowchart illustrating the method of controlling the thermotherapeutic treatment apparatus having the function of measuring a heart rate according to the embodiment of the present invention.

A method 200 of controlling the thermotherapeutic apparatus having the function of measuring a heart rate includes inputting user information and operation settings (S201), calculating a heart rate by using a ballistocardiogram signal (S202 to S204), actively performing a massage mode according to the heart rate (S206 to S209), and performing a sleep mode when a user is asleep (S210 to S212).

In more detail, as shown in FIG. 6, first, through the control device 100 of the thermotherapeutic apparatus, at least one of the user information and the operation settings is input by the user (S201). Here, the input user information may include an age and gender. Also, the operation settings may be a massage mode. Here, at least one of a massage pattern, a massage level, and a massage temperature may be set.

Next, the control device 100 of the thermotherapeutic apparatus senses a ballistocardiogram by using the weight detecting sensor 18 (S202). Here, the sensed signal may be a weight signal including a micro ballistocardiogram signal.

Next, the control device 100 of the thermotherapeutic apparatus performs a pretreatment for removing noise from the sensed ballistocardiogram signal (S203). Here, since the ballistocardiogram signal detected by the weight detecting sensor 18 is a micro signal included in a weight signal, not only power noise but also the weight signal and other noise may be removed in order to extract the micro ballistocardiogram signal. Here, the ballistocardiogram signal sensed by the weight detecting sensor 18 may be repetitively amplified and filtered out.

Next, the control device 100 of the thermotherapeutic apparatus extracts a heartbeat signal from the pretreated signal (S204). Here, the pretreated signal may be sampled and filtered out and a peak signal may be detected so as to extract the heartbeat signal. Here, the peak signal may correspond to the heartbeat signal.

Next, the control device 100 of the thermotherapeutic apparatus extracts a heart rate on the basis of the extracted heartbeat signal (S205). Here, the heart rate may be calculated on the basis of the number of peak points of the heartbeat signal extracted for a certain period of time.

Here, the control device 100 of the thermotherapeutic apparatus may perform control such that massage is automatically initiated according to whether the heart rate is calculated. Here, a state in which objects having a certain weight are disposed on the thermotherapeutic apparatus 10 may be distinguished from a state in which a human being lies down thereon according to sensing of the heart rate. Accordingly, lying of the user on the thermotherapeutic apparatus 10 to receive a massage may be precisely determined and the massage may be automatically initiated.

Next, the control device 100 of the thermotherapeutic apparatus determines a massage mode according to the calculated heart rate (S206). Here, a state of the user according to the heart rate may be determined and a massage mode capable of relaxing the state of the user may be automatically set. Here, it is possible to perform control such that a massage pattern, a massage level, and a massage temperature of the corresponding massage mode are automatically set to activate a sympathetic nervous system or a parasympathetic nervous system, and the corresponding massage mode is actively performed.

As a result of operation S206, when the calculated heart rate is within a range of a reference heart rate according to an age and gender of the user input by the user, the control device 100 of the thermotherapeutic apparatus performs a standard mode in which a massage mode set immediately prior is executed (S207).

Here, to use the thermotherapeutic apparatus 10, a massage and a thermal therapy may be performed in a massage mode set by a current user or a massage mode set by a previous user.

As a result of operation S206, when the calculated heart rate is more than the reference heart rate according to the age and gender of the user input by the user, the control device 100 of the thermotherapeutic apparatus performs a parasympathetic-stimulating mode which activates a parasympathetic nervous system of the user to stabilize body rhythms thereof (S208). Here, the reference heart rate may be a resting heart rate with respect to the input age and gender.

Here, the massage temperature may be set to be a first reference temperature to activate the parasympathetic nervous system.

Also, the massage pattern and the massage level may be set to be a massage pattern and a massage level which are preset to stimulate the parasympathetic nervous system. As an example, the massage pattern may be set to intensively massage a natal part (an end of a spinal cord) and a back part of a neck (a midbrain, a bulb of the spinal cord, and the like). Here, the natal part corresponds to the end of the spinal cord, and the back part of the neck corresponds to the midbrain or the bulb of the spinal cord in which the parasympathetic nervous system is located. Accordingly, the part is massaged such that the parasympathetic nervous system may be stimulated. Here, the massage level may be set such that a massage level around the back of the neck is lower than a massage level around the natal part.

As a result of operation S206, when the calculated heart rate is less than the reference heart rate according to the age and gender of the user input by the user, the control device 100 of the thermotherapeutic apparatus performs a sympathetic-stimulating mode which activates a sympathetic nervous system of the user to activate body rhythms thereof (S209).

Here, the massage temperature may be set to be a second reference temperature to activate the sympathetic nervous system.

Also, the massage pattern and the massage level may be set to be a massage pattern and a massage level which are preset to stimulate the sympathetic nervous system. As an example, the massage pattern may be set to intensively massage a spine (a middle of the spinal cord). Here, the spine corresponds to the middle of the spinal cord in which the sympathetic nervous system is located. Accordingly, the corresponding part is massaged such that the sympathetic nervous system may be stimulated. Also, the same massage level may be set with respect to a massaged part.

Here, in operations S207 to S209, the control device 100 of the thermotherapeutic apparatus may control the driving module 13 and the transfer motor 14 to perform a massage mode determined according to a heart rate of the user.

Next, the control device 100 of the thermotherapeutic apparatus determines whether a massage is continuously performed (S210) and finishes a massage operation when it is determined that the massage is not continuously performed.

As a result of determination in operation S210, when it is determined that the massage is continuously performed, the control device 100 of the thermotherapeutic apparatus determines whether the user is asleep on the basis of the heart rate calculated while performing the massage (S211). As an example, when the heart rate calculated while performing the massage is reduced to a certain level, it may be determined that the user is asleep.

As a result of determination in operation S211, when it is determined that the user is not asleep, the control device 100 of the thermotherapeutic apparatus continuously performs a currently set massage mode. Here, it is possible to return to operation S206, and the massage mode according to the heart rate may be continuously performed.

As a result of determination in operation S211, when it is determined that the user is asleep, the control device 100 of the thermotherapeutic apparatus performs a sleep mode which induces a deep sleep (S212). Here, the massage temperature, the massage pattern, and the massage level may be set to be a massage temperature, a massage pattern, and a massage level which are preset to induce a deep sleep.

As an example, the massage temperature may be set to be the second reference temperature, the massage level may be set to be lower than a massage level immediately prior, and the massage pattern may be set to maintain a massage pattern immediately prior or to be a massage pattern of the parasympathetic-stimulating mode.

Here, after a certain period of time has passed, the sleep mode may be terminated. Also, when the massage pattern immediately prior is maintained, the sleep mode may be terminated after a residual time of the corresponding massage pattern has passed. Accordingly, the thermotherapeutic apparatus 10 may terminate a massage operation.

Here, a massage temperature, a massage pattern, and a massage level which are preset for each performance mode have been described as corresponding to a massage mode prestored in the storage 140 but are not limited thereto and may be directly set by the user through the setting portion 17.

Through the method according to the embodiment of the present invention, since it is possible to relax a current state of the user, a massage may be actively performed. Also, since the presence of a user may be precisely determined in comparison to a case of determining the presence of a human being by using only a weight thereof, an unnecessary malfunction may be prevented.

The above-described method may be performed by the control device 100 or the mode performer 130 of the thermotherapeutic apparatus as shown in FIG. 3, and particularly, may be embodied as a software program which executes the above operations. In this case, such programs may be stored in a computer-readable recording medium or may be transmitted by a computer data signal combined with a carrier wave in a transmission medium or a communication network.

Here, the computer-readable recording medium includes all types of recording media in which data readable by a computer system is stored and, for example, may be a read-only memory (ROM), a random-access memory (RAM), a compact disc (CD)-ROM, a digital versatile disc (DVD)-ROM, a DVD-RAM, a magnetic tape, a floppy disk, a hard disk, an optical data storage device, and the like.

According to the embodiment of the present invention, a device and a method for controlling a thermotherapeutic apparatus having a function of measuring a heart rate may relax a current state of a user by automatically determining a massage mode according to a heart rate of the user so as to actively perform a massage.

Also, since whether a user is present is determined according to whether a heart rate is calculated, whether the user is present may be more precisely determined in comparison to a case of determining whether a human being is present by using only a weight thereof such that an unnecessary malfunction may be prevented.

Although one embodiment of the present invention has been described above, the concept of the present invention is not limited to the embodiment disclosed herein. Another embodiment may be easily perceived by one of ordinary skill in the art by adding, changing, deleting, adding, and the like a component within an equivalent range of the concept and should be included in the scope of the present invention.

What is claimed is:

1. A control device of a thermotherapeutic apparatus having a function of measuring a heart rate, the control device comprising:
 a weight detecting sensor which is configured to sense a weight signal including a weight of a user and a ballistocardiogram signal of the user;
 a pretreatment unit which is configured to extract the ballistocardiogram signal by removing a signal corresponding to the weight of the user from the weight signal, thereby obtaining a pretreated signal;
 a heartbeat signal extracting unit which is configured to extract a heartbeat signal from the pretreated signal obtained by the pretreatment unit; and
 a mode performing unit configured to perform a parasympathetic-stimulating mode which sets a massage temperature as a first reference temperature, and sets a massage pattern and a massage level as a first massage pattern and a first massage level, which are preset to stimulate the parasympathetic nervous system by massaging a natal and a back part of a neck of the user when a calculated heart rate is more than a reference heart rate according to an age and gender of the user,
 wherein the mode performing unit is configured to perform a sympathetic-stimulating mode which sets the massage temperature as a second reference temperature, and sets the massage pattern and the massage level as a second massage pattern and a second massage level, which are preset to stimulate the sympathetic nervous system when the calculated heart rate is less than the reference heart rate, and
 wherein the mode performing unit is configured to calculate the calculated heart rate on the basis of the extracted heartbeat signal.

2. The control device of claim 1, further comprising:
 a setting unit which is configured to set at least one of user information and operation settings is set; and
 a storage unit which is configured to store the reference heart rate and the massage temperature, the massage pattern, and the massage level according to each of the sympathetic-stimulating mode and the parasympathetic-stimulating mode, respectively,
 wherein the user information comprises an age and gender.

3. The control device of claim 2, wherein the mode performing unit is configured to perform the parasympathetic-stimulating mode, which massages the natal part and the back part of the neck of the user,
 wherein the mode performing unit is configured to perform the sympathetic-stimulating mode, which massages a spine of the user,
 wherein the mode performing unit is configured to perform a standard mode which operates in a state set by the setting unit immediately prior to when the calculated heart rate is equal to the reference heart rate, and wherein the mode performing unit is configured to control a driving module and a transfer motor to perform each of the sympathetic-stimulating and the parasympathetic-stimulating modes.

4. The control device of claim 2, wherein the mode performing unit is configured to determine whether the user is asleep on the basis of the calculated heart rate while performing the massage and controls a driving module and a transfer motor to perform a sleep massage mode which induces a deep sleep by setting the massage temperature, the massage pattern, and the massage level to be a temperature, a pattern, and level which are preset for inducing a deep sleep when it is determined that the user is asleep.

5. The control device of claim 1, wherein the pretreatment unit is configured to repetitively amplify and filter out the ballistocardiogram signal to obtain the pretreated signal, and wherein the heartbeat signal extracting unit is configured to extract the heartbeat signal by sampling and filtering out the pretreated signal.

6. A method of controlling a thermotherapeutic apparatus having a function of measuring a heart rate, the method comprising:
sensing a weight signal including a weight of a user and a ballistocardiogram signal of the user;
extracting the ballistocardiogram signal by removing a signal corresponding to the weight of the user from the weight signal;
pretreating the extracted ballistocardiogram signal;
extracting a heartbeat signal from a pretreated signal in the pretreating;
calculating a heart rate on the basis of the extracted heartbeat signal;
determining a massage mode for one of a parasympathetic-stimulating mode and a sympathetic-stimulating mode according to the calculated heart rate; and
controlling the thermotherapeutic apparatus to perform the determined massage mode,
wherein the controlling comprises setting a massage temperature as a first reference temperature, and setting a massage pattern and a massage level as a first massage pattern and a first massage level which are preset to stimulate the parasympathetic nervous system by massaging a natal and a back part of a neck of the user when the calculated heart rate is more than a reference heart rate according to an age and gender of a user if the determined massage mode is the parasympathetic-stimulating mode,
setting the massage temperature as a second reference temperature, and setting the massage pattern and the massage level as a second massage pattern and a second massage level which are preset to stimulate the sympathetic nervous system when the calculated heart rate is less than the reference heart rate if the determined massage mode is the sympathetic-stimulating mode.

7. The method of claim 6, further comprising inputting at least one of user information and operation settings, wherein the user information comprises the age and gender.

8. The method of claim 7, wherein the controlling comprises:
performing the parasympathetic-stimulating which massages the natal part and the back part of the neck of the user;
performing the sympathetic-stimulating which massages a spine of the user; and
performing a standard mode which operates in a state set in the controlling immediately prior to when the calculated heart rate is equal to the reference heart rate, and
wherein each performing operation comprises controlling a driving module and a transfer motor to perform the determined massage mode.

9. The method of claim 7, further comprising:
determining whether the user is asleep on the basis of the calculated heart rate while performing a massage; and
controlling to perform a sleep mode which induces a deep sleep by setting the massage temperature, the massage pattern, and the massage level to be a temperature, pattern, and level which are preset for inducing a deep sleep when it is determined that the user is asleep.

10. The method of claim 6, wherein the pretreating comprises repetitively amplifying and filtering out the ballistocardiogram signal to obtain the pretreated signal, and wherein the extracting comprises extracting the heartbeat signal by sampling and filtering out the pretreated signal.

* * * * *